United States Patent [19]
Zajacek et al.

[11] Patent Number: 5,384,418
[45] Date of Patent: Jan. 24, 1995

[54] INTEGRATED PROCESS FOR EPOXIDE PRODUCTION

[75] Inventors: John G. Zajacek, Devon; John C. Jubin, Jr., West Chester, both of Pa.; Guy L. Crocco, Wilmington, Del.

[73] Assignee: Arco Chemical Technology, L.P., Greenville, Del.

[21] Appl. No.: 241,215

[22] Filed: May 10, 1994

Related U.S. Application Data

[63] Continuation-in-part of Ser. No. 186,716, Jan. 25, 1994, abandoned.

[51] Int. Cl.$^6$ .................. C07D 301/12; C07D 303/04
[52] U.S. Cl. .................................................. 549/531
[58] Field of Search ........................................ 549/531

[56] References Cited

U.S. PATENT DOCUMENTS

| | | |
|---|---|---|
| 3,592,776 | 7/1971 | Fletcher et al. ............... 549/531 |
| 3,953,362 | 4/1976 | Lines et al. |
| 4,009,122 | 2/1977 | Lines et al. |
| 4,157,346 | 6/1979 | Lines et al. |
| 4,824,976 | 4/1989 | Clerici et al. |
| 4,833,260 | 5/1989 | Neri et al. |
| 4,937,216 | 6/1990 | Clerici et al. |
| 5,166,372 | 11/1992 | Crocco et al. ............... 549/531 |
| 5,214,168 | 5/1993 | Zajacek et al. ............... 549/531 |
| 5,221,795 | 6/1993 | Clerici et al. |
| 5,252,758 | 10/1993 | Clerici et al. |
| 5,262,550 | 11/1993 | Crocco et al. |

FOREIGN PATENT DOCUMENTS 93108847 12/1993
2166636 2/1992 Japan.

OTHER PUBLICATIONS

Mario G. Clerici et al.-Epoxidation of Lower Olefins with Hydrogen Peroxide & Titanium Silicalite-Sep. 4, 1992-Journal of Catalysis, 140-pp. 71-83 (1993).
Notari-Studies in Surface Science, and Catalysis, vol. 32 (1988) pp. 413-425.
M. G. Clerici et al.-Synthesis of Propylene Oxide from Propylene and Hydrogen Peroxide Catalized by Titanium Silicalite, Chemtracts-Inorganic Chemistry Date 1991 pp. 344-346.
Journal of Catalyst-M. G. Clerici et al 129(1991) Synthesis of Proplylene Oxide from Propylene & Hydrogen Peroxide Catalyized by Titanium Silicalite pp. 159-167.
D. R. C. Huybrects et al. Catalysis Letters 8(1991) Factors Influencing the Catalytic Activity of Titanium Silicalites in Selective Oxidation pp. 237-244.
Takashi Tatsumi et al.-Shape Selective Epoxidation of Alkenes Catalyzed by Titanosilicate-Chemistry Letter (1990) pp. 297-298 The Chemical Society of Japan.

*Primary Examiner*—Joseph E. Evans
*Attorney, Agent, or Firm*—Stephen D. Harper

[57] ABSTRACT

Epoxides are produced by an integrated process involving molecular oxygen oxidation of an aliphatic secondary alcohol, separation of the ketone co-product, epoxidation of an ethylenically unsaturated substrate by the substantially ketone-free oxidation product in the presence of a titanium silicalite catalyst, and regeneration of the secondary alcohol by hydrogenation of the ketone co-product.

12 Claims, 1 Drawing Sheet

INTEGRATED PROCESS FOR EPOXIDE PRODUCTION

This is a continuation-in-part of application Ser. No. 08/186,716, filed Jan. 25, 1994, now abandoned.

FIELD OF THE INVENTION

This invention relates to an integrated process for producing an epoxide wherein the only reactants consumed in the overall process are an ethylenically unsaturated substrate, molecular oxygen, and hydrogen. In particular, the invention pertains to a process whereby an oxidant mixture comprised of an aliphatic secondary alcohol, a ketone corresponding to the secondary alcohol, and hydrogen peroxide, is generated by reaction of the alcohol with molecular oxygen, subjected to a separation step (preferably, distillation) to remove substantially all of the ketone and then reacted with an ethylenically unsaturated substrate in the presence of a titanium silicalite catalyst. The recovered ketone is recycled back to alcohol by hydrogenation; the secondary alcohol which serves as a solvent for the epoxidation step is likewise recovered and resubjected to molecular oxygen oxidation.

BACKGROUND OF INVENTION

Many different methods for the preparation of epoxides have been developed. One such method involves the use of certain titanium silicalite materials to catalyze olefin oxidation by hydrogen peroxide. This method is described, for example, in Huybrechts et al., *J. Mol. Catal.* 71, 129 (1992), U.S. Pat. Nos. 4,824,976 (Clerici et al.) and 4,833,260 (Neri et al.), European Pat. Pub. Nos. 311,983, 190,609, 315,247 and 315,248, Belgian Pat. Pub. No. 1,001,038, Clerici et al., *J. Catal.* 129,159(1991), and Notari, in "Innovation in Zeolite Material Science," *Studies in Surface Science and Catalysts,* vol. 37, p. 413 (1988).

However, the outcome of synthetic reactions catalyzed by titanium silicalites is highly unpredictable and seemingly minor changes in reactants and conditions may drastically change the type of product thereby obtained. For example, when an olefin is reacted with hydrogen peroxide in the presence of titanium silicalite the product obtained may be either epoxide (U.S. Pat. No. 4,833,260), glycol ether (U.S. Pat. No. 4,476,327), or glycol (Example 10 of U.S. Pat. No. 4,410,501).

The prior art related to titanium silicalite-catalyzed epoxidation teaches that it is beneficial to employ a hydrogen peroxide solution that does not contain large amounts of water and recommends the use of an organic solvent as a liquid medium for the epoxidation reaction. Suitable solvents are said to include polar compounds such as alcohols, ketones, ethers, glycols, and acids. Solutions in tert-butanol, methanol, acetone, acetic acid, and propionic acid are taught to be most preferred. However, hydrogen peroxide is currently available commercially only in the form of aqueous solutions. To employ one of the organic solvents recommended by the prior art, it will thus be necessary to exchange the water of a typical hydrogen peroxide solution for the organic solvent. This will necessarily increase greatly the overall costs associated with an epoxidation process of this type. Additionally, concentration of hydrogen peroxide to a pure or nearly pure state is exceedingly dangerous and is normally avoided. Thus, it will not be practicable or cost-effective to simply remove the water by distillation and replace it with the organic solvent. Since hydrogen peroxide has a high solubility in and high affinity for water, liquid-liquid extraction of hydrogen peroxide from an aqueous phase to an organic phase will not be feasible. Moreover, many of the solvents taught by the prior art to be preferred for epoxidation reactions of this type such as tert-butanol, acetone, and methanol are water miscible and thus could not be used in such an extraction scheme. An epoxidation process wherein a readily obtained oxidant solution containing hydrogen peroxide and an organic solvent which promotes high yields of epoxide products is employed would thus be of significant economic advantage.

U.S. Pat. No. 5,214,168 proposes an integrated process for epoxide production wherein an aryl-substituted secondary alcohol such as alpha methyl benzyl alcohol is oxidized with molecular oxygen to provide the hydrogen peroxide used in a subsequent epoxidation step. While this process works well when practiced in a batch type mode, it has now been found that certain of the titanium silicalites employed as epoxidation catalysts experience deactivation when such a process is run on a continuous basis. This deterioration in activity and selectivity is believed to be due to the accumulation of oligomeric and polymeric by-products derived from the aryl-substituted secondary alcohol or other species present in the epoxidation reaction mixture. While the deactivated catalyst could be regenerated using known techniques such as solvent washing and/or recalcination, it would be highly advantageous to develop a continuous integrated epoxidation process wherein less frequent catalyst regeneration or replacement is needed.

Example 35 of U.S. Pat. No. 4,833,260 describes a procedure wherein propylene is converted to propylene oxide. An isopropanol/water mixture is reacted with oxygen at 135° C. to afford a mixture containing hydrogen peroxide. The mixture is thereafter used directly in a titanium silicalite-catalyzed epoxidation of propylene without intervening treatment or fractionation. The temperature during epoxidation is carefully maintained at 20° C. by means of a constant temperature bath. Due to the highly exothermic nature of the olefin epoxidation reaction, it is quite difficult to maintain a reaction of this type at room temperature or lower, especially if practiced on a large scale. Even if an effective means of removing heat from the reaction mixture is employed, the utility (cooling) costs associated with such an arrangement will place the process at a distinct competitive disadvantage relative to conventional epoxidation processes. It would thus be highly desirable to be able to operate a titanium silicalite-catalyzed epoxidation using a secondary alcohol-derived hydrogen peroxide stream at superambient temperatures without a significant selectivity penalty.

Another problem associated with the use of an oxidized isopropanol mixture as a source of hydrogen peroxide in a olefin epoxidation reaction catalyzed by titanium silicalite is the potential for forming significant quantities of organic peroxides from interaction of the hydrogen peroxide and the acetone generated by oxidation of the isopropanol. See, for example, Sauer et al., *J. Physical Chem.* 75, 3004–3011 (1971) and Sauer et al., ibid. 76, 1283–1288 (1972). These organic peroxides have been found to accumulate during isopropanol oxidation, during storage of the oxidate mixture, as well as during olefin epoxidation. The formation of such peroxide species detracts from the selective transformation of an ethylenically unsaturated substrate to epoxide since hydrogen peroxide is being consumed. In addition, the presence of the organic peroxides, some of which may be highly explosive in pure form, complicates the purification and separation steps following epoxidation.

SUMMARY OF THE INVENTION

This invention provides an integrated process for producing an epoxide comprising the steps of (a) contacting an aliphatic secondary alcohol selected from isopropanol and sec-butanol with molecular oxygen in a liquid phase at a temperature of 50° to 200° C. to form an oxidant mixture comprised of 40 to 90 weight percent aliphatic secondary alcohol, 5 to 35 weight percent of an aliphatic ketone corresponding to said aliphatic secondary alcohol, 1 to 20 weight percent hydrogen peroxide, and 0 to 35 weight percent water;

(b) separating substantially all of the aliphatic ketone from the oxidant mixture so as to provide a hydrogen peroxide-containing stream comprised of hydrogen peroxide, aliphatic secondary alcohol, less than 1 weight percent aliphatic ketone and less than 0.5 weight percent aliphatic ketone peroxides;

(c) reacting the overhead stream with hydrogen in the presence of a heterogeneous hydrogenation catalyst wherein said hydrogenation catalyst is comprised of a transition metal selected from palladium, platinum, ruthenium, chromium, rhodium, and nickel at a temperature of 20° to 175° C. and a hydrogen pressure of 0.5 to 100 atmospheres to convert the aliphatic ketone in the overhead stream to the aliphatic secondary alcohol and recycling at least a portion of the aliphatic secondary alcohol for use in step (a);

(d) contacting the hydrogen peroxide-containing stream with an ethylenically unsaturated substrate and a catalytically effective amount of a titanium silicalite at a temperature of from 40° C. to 120° C., wherein the molar ratio of substrate:hydrogen peroxide is from 1:2 to 10:1, to form an epoxidation reaction mixture comprised of aliphatic secondary alcohol, epoxide, and water; and (e) separating the aliphatic secondary alcohol present in the epoxidation reaction mixture from the epoxide and recycling at least a portion of the aliphatic secondary alcohol thereby obtained for use in step (a).

DETAILED DESCRIPTION OF THE INVENTION

Figure 1:
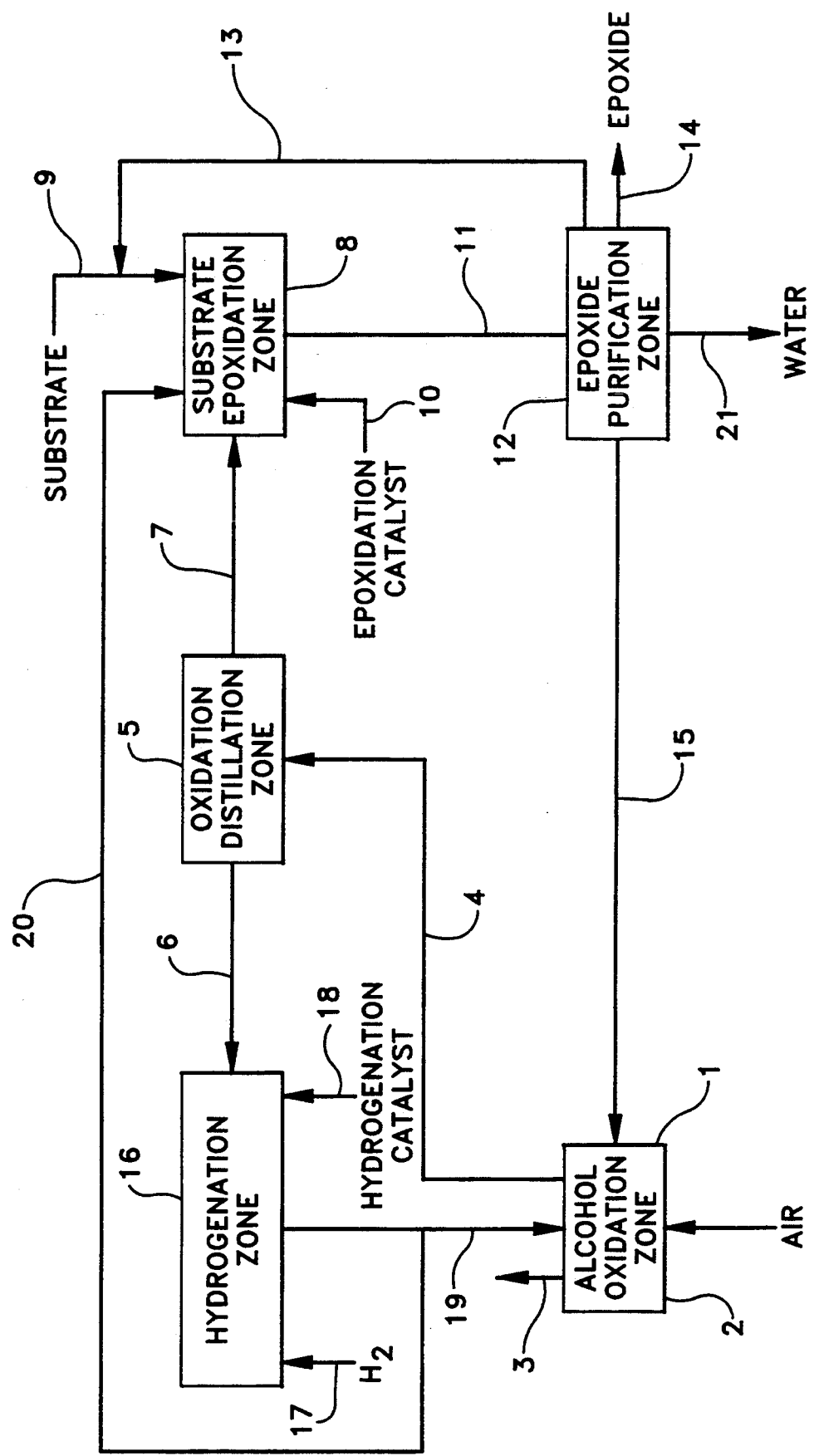
FIG. 1 illustrates in schematic form a suitable embodiment of the process of the invention.

It has now been surprisingly discovered that exceptionally high yields of epoxide are conveniently and economically realized through the utilization of an integrated process wherein a crude oxidant mixture generated by molecular oxygen oxidation of a secondary alcohol is subjected to a fractionation so as to remove substantially all of the ketone co-product produced by oxidation and to minimize the accumulation of ketone peroxide species prior to use in an epoxidation step. The recovered ketone co-product is readily converted in whole or in part by hydrogenation back to alcohol for a further oxidation/epoxidation cycle. Likewise, the aliphatic secondary alcohol which serves as a reaction medium during epoxidation is separated from the desired epoxide product by fractional distillation and reused.

We have unexpectedly found that significant advantages are realized when the aliphatic ketone is removed from the oxidant mixture prior to the use of that mixture as a source of hydrogen peroxide in a titanium silicalite-catalyzed epoxidation step at a reaction temperature of 40° C. or higher. This finding was unexpected in view of the fact that the prior art teaches that ketones such as acetone are preferred epoxidation solvents when using hydrogen peroxide and a titanium silicalite catalyst. Removal of the aliphatic ketone effectively reduces the amount of hydrogen peroxide lost during epoxidation due to formation of by-products. Moreover, such removal has been found to be effective in liberating hydrogen peroxide from any peroxides generated during air oxidation of the secondary alcohol or subsequent storage. Excellent selectivity to epoxide based on hydrogen peroxide is thereby realized with minimal losses due to aliphatic ketone peroxide. In this context, the term "aliphatic ketone peroxides" includes those organic compounds derived from interaction of the aliphatic ketone and hydrogen peroxide which contain at least one —O—O—group (see the aforementioned articles by Sauer et al.).

Another surprising aspect of the process of the invention is that high selectivity to epoxide is attained in spite of the fact that substantial amounts of secondary alcohol are present during epoxidation. The prior art teaches that primary and secondary alcohols such as isopropanol are readily oxidized to the corresponding aldehydes and ketones by reacting with hydrogen peroxide in the presence of titanium silicalite (U.S. Pat. No. 4,480,135; van der Pol et al., Applied Catalysis A: General 106, 97–113(1993); Notari, J.Catal 146. 476 (1994). It has now been discovered that only minimal oxidation of secondary alcohol to the corresponding ketone takes place during epoxidation, despite the fact that both ethylenically unsaturated substrates and alcohols are known to react with hydrogen peroxide in the presence of titanium silicalite and thus would be expected to compete for the available active oxygen. The finding that nearly all of the hydrogen peroxide reacts selectively with the substrate and not (to any significant degree) with the secondary alcohol was thus quite unexpected.

The overall process of this invention may thus be represented as follows:

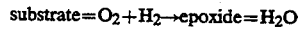

substrate+$O_2$+$H_2$→epoxide+$H_2O$ wherein the epoxide is the only organic species produced (other than minor quantities of by-products) and the ethylenically unsaturated substrate is the only organic species consumed. The process is consequently exceedingly attractive from a commercial point of view.

The secondary aliphatic alcohols suitable for use include isopropanol (isopropyl alcohol) and sec-butanol (sec-butyl alcohol).

The secondary aliphatic alcohol is reacted with molecular oxygen from a suitable source such as air to yield the oxidant mixture, which will typically contain excess secondary aliphatic alcohol, the aliphatic ketone resulting from oxidation of the secondary alcohol and having the same hydrocarbon skeleton as the alcohol, hydrogen peroxide, and water. The starting material to be oxidized may contain minor amounts of the aliphatic ketone and/or water in addition to the alcohol. For example, the azeotrope of water and isopropanol (87 wt % isopropanol, 12.2 wt % water) may be used to advantage. Generally speaking, the oxidation conditions are adjusted so as to yield an oxidant mixture comprised of 40 to 90 weight percent aliphatic secondary alcohol, from about 1 to 20 weight percent hydrogen peroxide, 5 to 35 weight percent of the aliphatic ketone, and 0 to 35 weight percent water. Partial conversion of the secondary alcohol is accomplished (e.g., from 5 to 50%) such that the unreacted secondary alcohol may be utilized as a carrier or solvent for the hydrogen peroxide and substrate during epoxidation. Residence, hold-up or reaction times of from about 0.25 hours to 4 hours will typically be sufficient for this purpose. The oxidation may be either uncatalyzed or catalyzed (for example, by introduction of a minor amount of a peroxide or hydroperoxide such as t-butyl hydroperoxide), but is most preferably carried out under the conditions described in U.S. Pat. Nos. 2,871,102, 2,871,103, and 2,871,104 and British Pat. Nos. 758,907 and 1,421,499 (the teachings of these patents are incorporated herein by reference in their entirety). Temperatures of from 50° to 200° C. (more preferably, from 100 to 180° C.) will typically be appropriate for use in order to attain reasonable oxidation rates. The preferred range of oxygen partial pressure in the feed gases (which may include an inert diluent gas such as nitrogen in addition to oxygen) is 5 to 500 psia (more preferably, 15 to 250 psia) partial pressure. Total pressure in the oxidation reaction zone should be sufficient to maintain the components of the reaction mixture in the liquid phase (50 psia to 1000 psia is normally sufficient). A plurality of oxidation reaction zones maintained at different temperatures may be employed, as described in British Pat. No. 758,907. The alcohol oxidation may be performed in a continuous manner using, for example, a continuous stirred tank reactor (CSTR). Although a hydrogen peroxide stabilizer could be added to the oxidation reaction zone, it is critical that the stabilizer selected for use not interfere with the subsequent epoxidation step. For example, high levels of alkali metal pyrophosphates have been found to poison the titanium silicalite epoxidation catalyst.

Prior to use in the epoxidation step of this process, it is critical that the aliphatic ketone is substantially separated or removed from the oxidant mixture. Any known separation method or technique which is suitable for this purpose may be utilized, including fractionation procedures.

Preferably, however, the oxidant mixture is fractionally distilled whereby the secondary aliphatic ketone is vaporized and removed from the oxidant mixture as an overhead stream. The hydrogen peroxide-containing stream obtained by such a procedure thus may comprise a bottoms fraction. Such fractionation may be facilitated by the application of heat and/or reduced (subatmospheric) pressure. The aliphatic ketone concentration in the bottoms fraction thereby produced must be less than 1 weight percent (more preferably, less than 0.5 weight percent). To minimize the formation of any ketone/hydrogen peroxide adducts having peroxy character, this separation is most preferably performed directly after molecular oxygen oxidation. Thus, the oxidant mixture exiting from the oxidizer zone is preferably taken into a distillation column without intervening storage or retention. To accomplish rapid and complete removal of the aliphatic ketone from the oxidant mixture, it may be desirable to also take overhead some portion of the secondary alcohol and/or water. In one embodiment, for example, the overhead stream may comprise 10 to 80 mole % ketone, 15 to 60 mole % secondary alcohol, and 5 to 30 mole % water. However, for safety reasons, care must be taken not to overly concentrate the hydrogen peroxide in the bottoms fraction nor to have any appreciable amount of hydrogen peroxide in the overhead stream. The residence time in the distillation step is also critical. The residence time must be sufficient to accomplish substantial reversal of any ketone/hydrogen peroxide reaction products generated during molecular oxygen oxidation or thereafter to bring the level of aliphatic ketone peroxides to less than 0.5 weight percent total. Excessive residence time should be avoided, however, to avoid decomposition of the hydrogen peroxide. In one preferred embodiment of the invention, a residence time of 10 to 45 minutes (more preferably, 15 to 30 minutes) at 90° to 130° C. (more preferably, 100° to 120° C.) is employed. Under these conditions, it has been found that the desired removal of ketone and conversion of any ketone peroxides present may be readily achieved with minimal loss of the hydrogen peroxide in the oxidant mixture. Improved results may be obtained by carefully passivating the distillation column and/or treating the oxidant mixture so as to remove or counteract any species which might catalyze the decomposition of hydrogen peroxide or formation of ketone peroxides. Extractive distillation techniques may also be advantageously used. Other separation procedures capable of reducing the aliphatic ketone content of the oxidant mixture without significant loss of the hydrogen peroxide contained therein may also be used including, for example, absorption, countercurrent extraction, membrane separation, and the like. Fractionation techniques wherein multiple stages are employed are especially suitable.

In the epoxidation step of the process of this invention, the hydrogen peroxide-containing stream obtained following separation of aliphatic ketone from the oxidant mixture is contacted with an ethylenically unsaturated substrate and a catalytically effective amount of a titanium silicalite at a temperature of from 40° C. to 120° C. to convert the substrate to the desired epoxide.

The ethylenically unsaturated substrate epoxidized in the process of this invention is preferably an organic compound having from two to ten carbon atoms and at least one ethylenically unsaturated functional group (i.e., a carbon-carbon double bond) and may be a cyclic, branched or straight chain aliphatic olefin. More than one carbon-carbon double bond may be present in the olefin; dienes, trienes, and other polyunsaturated substrates thus may be used.

Exemplary olefins suitable for use in the process of this invention include ethylene, propylene, the butenes, butadiene, the pentenes, isoprene, 1-hexene, 3-hexene, 1-heptene, 1-octene, diisobutylene, 1-nonene, the trimers and tetramers of propylene, cyclopentene, cyclohexene, cycloheptene, cyclooctene, cyclooctadiene, dicyclopentadiene, methylenecyclopropane, methylenecyclopentane, methylenecyclohexane, vinylcyclohexane, and vinyl cyclohexene.

Mixtures of olefins may be epoxidized and the resulting mixture of epoxides either employed in mixed form or separated into the different component epoxides.

The process of this invention is especially useful for the epoxidation of $C_2$-$C_{10}$ olefins having the general structure

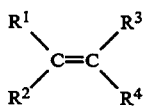

wherein $R^1$, $R^2$, $R^3$, and $R^4$ are the same or different and are selected from the group consisting of hydrogen and $C_1$-$C_8$ alkyl (selected so that the total number of carbons in the olefin does not exceed 10).

The process of this invention is also suitable for use in epoxidizing ethylenically unsaturated substrates containing functional groups other than aliphatic hydrocarbyl moieties. For example, the carbon-carbon double bond can be substituted with groups such as —$CO_2H$, —$CO_2R$, —CN, or —OR wherein R is an alkyl, cycloalkyl, aryl or aralkyl substituent. The radicals $R^1$, $R^2$, $R^3$, and $R^4$ in the structural formula shown hereinabove may contain aryl, aralkyl, halo, nitro, sulfonic, cyano, carbonyl (e.g., ketone, aldehyde), hydroxyl, carboxyl (e.g., ester, acid) or ether groups. Examples of ethylenically unsaturated substrates of these types include allyl alcohol, styrene, allyl chloride, allyl methyl ether, allyl phenyl ether, methyl methacrylate, acrylic acid, methyl acrylate, stilbene, and the like.

The amount of hydrogen peroxide relative to the amount of ethylenically unsaturated substrate is not critical, but most suitably the molar ratio of substrate:hydrogen peroxide is from about 100:1 to 1:10 when the substrate contains one ethylenically unsaturated group. The molar ratio of ethylenically unsaturated groups in the substrate to hydrogen peroxide is more preferably in the range of from 1:2 to 10:1 (most preferably, 1:1 to 5:1). One equivalent of hydrogen peroxide is theoretically required to oxidize one equivalent of a mono-unsaturated substrate, but it may be desirable to employ an excess of substrate to optimize selectivity to the epoxide. A key advantage of the process of this invention as compared to other epoxidation processes is that a large molar excess of substrate relative to hydrogen peroxide is not required. High yields of epoxide may be realized using a slight (i.e., 5-90%) molar excess of substrate relative to hydrogen peroxide (i.e., the molar ratio of substrate to hydrogen peroxide is from 1.05:1 to 1.9:1). The hydrogen peroxide is thus used in a very efficient manner; little of the hydrogen peroxide is wasted through non-selective decomposition to water (i.e., without oxidation of a substrate molecule). Since hydrogen peroxide is relatively costly to generate, this means that the overall integrated process of the invention may be economically practiced on a commercial scale. Additionally, processing costs arising from recovery and recycling of substrate are minimized since there is no need to employ a large excess of substrate in order to optimize epoxide selectivity, in contrast to known epoxidation processes employing organic hydroperoxides and molybdenum-containing catalysts.

The titanium silicalites useful as catalysts in the epoxidation step of the process comprise the class of zeolitic substances wherein titanium is substituted for a portion of the silicon atoms in the lattice framework of a silicalite molecular sieve. Such substances are well-known in the art and are described, for example, in U.S. Pat. No. 4,410,501 (Taramasso et al.), U.S. Pat. No. 4,824,976 (Clerici et al.), U.S. Pat. No. 4,666,692 (Taramasso et al.), Thangaraj et al., *J. Catal.* 130, 1 (1991), Reddy et al., *Applied Catal.* 58, L-1 (1990), Reddy et al., *J. Catal.* 130, 440 (1991), Reddy et al., *Zeolites* 12, 95 (1992), Belgian Pat. Pub. No. 1,001,038 (Bellussi et al.), Huybrechts et al., *J. Mol. Catal.* 71,129 (1992), Huybrechts et al., *Catal. Letter* 8, 237 (1991), U.S. Pat. No. 4,656,016 (Taramasso et al.), U.S. Pat. No. 4,859,785 (Bellussi et al.), European Pat. Pub. No. 269,018 (Bellussi et al.), U.S. Pat. No. 4,701,428 (Bellussi et al.), U.S. Pat. No. 5,082,641 (Popa et al.), Clerici et al., *J. Catal.* 129,159 (1991), Bellussi et al., *J. Catal.* 133, 220 (1992), Szostak, *Molecular Sieves-Principles of Synthesis and Identification.* pp. 250-252 (1989), and Notari, "Synthesis and Catalytic Properties of Titanium Containing Zeolites", *Innovation in Zeolite Materials Science*, Grobet et al., Eds., 413 (1988). The teachings of these publications are incorporated herein by reference in their entirety.

Particularly preferred titanium silicalites include the classes of molecular sieves commonly referred to as "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Also suitable for use are the titanium-containing molecular sieves having framework structures isomorphous to zeolite beta which are described in U.S. applications Ser. Nos. 08/172,404 and 08/172,405, filed Dec. 23, 1993. The titanium silicalite preferably contains no metals other than titanium and silica in the lattice framework, although minor amounts of boron, iron, aluminum, and the like may be present.

Epoxidation catalysts suitable for use in the process of this invention will have a composition corresponding to the following empirical formula $xTiO_2:(1-x)SiO_2$, where x is between 0.0001 and 0.500. More preferably, the value of x is from 0.01 to 0.125. The molar ratio of Si:Ti in the lattice framework of the titanium silicalite is advantageously from 9.5:1 to 99:1 (most preferably, from 9.5:1 to 60:1). The use of relatively titanium-rich silicalites, such as those described in Thangaraj et al., *J. Catalysis* 130, 1-8 (1991), may also be desirable.

The amount of catalyst employed is not critical, but should be sufficient so as to substantially accomplish the desired epoxidation reaction in a practicably short period of time. The optimum quantity of catalyst will depend upon a number of factors including reaction temperature, substrate reactivity and concentration, hydrogen peroxide concentration, type and concentration of organic solvent as well as catalyst activity and the type of reactor or reaction system (i.e., batch vs. continuous) employed. In a batch-type or slurry reaction, for example, the amount of catalyst will typically be from 0.001 to 10 grams per mole of substrate. The concentration of titanium in the total epoxidation reaction mixture will generally be from about 10 to 10,000 ppm.

The catalyst may be utilized in powder, pellet, microspheric, extruded, monolithic or any other suitable physical form. The use of a binder (co-gel) or support in combination with the titanium silicalite may be advantageous. Supported or bound catalysts may be prepared by the methods known in the art to be effective for zeolite catalysts in general. Preferably, the binder or support is essentially non-acidic and does not catalyze the non-selective decomposition of hydrogen peroxide or ring-opening of the epoxide.

Illustrative binders and supports include silica, alumina, silica-alumina, silica-titania, silica-thoria, silicamagnesia, silica-zironia, silica-beryllia, and ternary compositions of silica with other refractory oxides. Also useful are clays such as montmorillonites, koalins, bentonites, halloysites, dickites, nacrites, and ananxites. The proportion of titanium silicalite:binder or support may range from 99:1 to 1:99, but preferably is from 5:95 to 80:20. The methods described in U.S. Pat. No. 4,701,428 (incorporated herein by reference in its entirety) may be adapted for the preparation of microspheres containing oligomeric silica binder and titanium silicalite crystals which are suitable for use in the process of this invention.

The catalyst may be treated with an alkaline (basic) substance or a silylating agent so as to reduce the surface acidity, as described in U.S. Pat. No. 4,937,216.

The epoxidation reaction temperature is critical and must be from 40° C. to 120° C., which in the process of this invention has been found to be sufficient to accomplish selective conversion of the ethylenically unsaturated substrate to epoxide within a reasonably short period of time with minimal non-selective decomposition of the hydrogen peroxide. It is generally advantageous to carry out the reaction to achieve as high a hydrogen peroxide conversion as possible, preferably at least 50%, more preferably at least 90%, most preferably at least 99%, consistent with reasonable selectivities. The optimum reaction temperature will be influenced by catalyst concentration and activity, substrate reactivity, reactant concentrations, and type of solvent employed, among other factors. Reaction or residence times of from about 10 minutes to 48 hours will typically be appropriate, depending upon the above-identified variables. The reaction is preferably performed at atmospheric pressure or at elevated pressure (typically, between 1 and 100 atmospheres). Generally, it will be desirable to maintain the reaction components as a liquid mixture. For example, when an olefin such as propylene is used having a boiling point at atmospheric pressure which is less than the epoxidation temperature, a superatmospheric pressure sufficient to maintain the desired concentration of propylene in the liquid phase must be utilized.

The epoxidation step of this invention may be carried out in a batch, continuous, or semi-continuous manner using any appropriate type of reaction vessel or apparatus such as a fixed bed, transport bed, stirred slurry, or CSTR reactor. Particularly preferred for use is the catalytic converter described in U.S. application Ser. No. 08/171,144, filed Dec. 20, 1993. Known methods for conducting metal-catalyzed epoxidations using hydrogen peroxide will generally also be suitable for use. Thus, the reactants may be combined all at once or sequentially. For example, the hydrogen peroxide and/or the substrate may be added incrementally to the reaction zone.

Once the epoxidation has been carried out to the desired degree of conversion, the epoxide product may be separated and recovered from the reaction mixture using any appropriate technique such as fractional distillation, extractive distillation, liquid-liquid extraction, crystallization, or the like. After separating from the epoxidation reaction mixture by any suitable method such as filtration (as when a slurry reactor is utilized, for example), the recovered titanium silicalite catalyst may be economically re-used in subsequent epoxidations. Where the catalyst is deployed in the form of a fixed bed, the epoxidation product withdrawn as a stream from the epoxidation zone will be essentially catalyst free with the catalyst being retained within the epoxidation zone. Similarly, any unreacted substrate or hydrogen peroxide may be separated and recycled or otherwise disposed of. In certain embodiments of the instant process where the epoxide is produced on a continuous basis, it may be desirable to periodically or constantly regenerate all or a portion of the used catalyst in order to maintain optimum activity and selectivity. Suitable regeneration techniques are well-known and include, for example, calcination and solvent treatment.

In the hydrogenation step, the ketone in the overhead stream is reacted with hydrogen in the presence of a transition metal hydrogenation catalyst under conditions effective to convert all or a portion of the ketone to the corresponding secondary aliphatic alcohol.

Methods of converting aliphatic ketones such as acetone and 2-butanone to their corresponding secondary aliphatic alcohols by catalytic hydrogenation using a transition metal catalyst and hydrogen gas are well-known and are generally described, for example, in the following publications (incorporated herein by reference in their entirety): Freifelder, *Catalytic Hydrogenation Organic Synthesis-Procedures and Commentary*, Wiley-Interscience (1978), Augustine, *Catalytic Hydrogenation Techniques and Applications in Organic Synthesis* M. Dekker (1965), Freifelder, *Practical Catalytic Hydrogenation: Techniques and Applications* Wiley-Interscience (1971), Keiboom, *Hydrogenation and Hydrogenolysis in Synthetic Organic Chemistry*, Delft University Press (1977), and Peterson, *Hydrogenation Catalysts*, Noyes Data Corp. (1977). The following publications (incorporated herein by reference in their entirety) provide examples of specific catalysts and reaction conditions capable of selectively and rapidly hydrogenating acetone to isopropanol: U.S. Pat. Nos. 2,999,075, 3,013,990, Jpn. Kokai 2-279,643 (*Chem. Abst.* 114: 142662p), Jpn. Kokai 3-141,235 (*Chem. Abst.* 115: 235194y), Jpn. Kokai 3-41,038 (*Chem. Abst.* 114: 228366g), Jpn. Kokai 62-12, 729 (*Chem. Abst.* 107: 6768f), and Jpn. Kokai 59-189,938 (*Chem. Abst.* 102: 138489x).

The transition metal in the hydrogenation catalyst is most preferably palladium, platinum, chromium (as in copper chromite, for example), rhodium, nickel, or ruthenium. If water is present in the overhead stream, the use of Raney nickel or molybdenum-promoted nickel is especially advantageous. The hydrogenation is suitably carried out in either a liquid or vapor phase.

The temperature, hydrogen pressure, and catalyst concentration during hydrogenation are selected so as to accomplish substantial (i.e., at least 80% and more preferably at least 98%) conversion of the ketone to secondary alcohol within a practicably short reaction time (i.e., approximately 15 minutes to 12 hours) without overreduction of the ketone to aliphatic compounds which do not contain hydroxyl groups. The optimum hydrogenation conditions will vary depending upon the type of catalyst selected for use and the reactivity of the ketone, but may be readily determined by one skilled in the art with minimal experimentation based on the known art pertaining to ketone hydrogenation. Typically, temperatures of from about 20° C. to 175° C. and hydrogen pressures of from about 0.5 to 100 atmospheres will be appropriate for use. Preferably, the molar ratio of $H_2$ to ketone is from about 1:1 to 4:1. The amount of catalyst employed is preferably sufficient to permit weight hourly space velocities of from 0.1 to 10 grams of ketone per gram of catalyst per hour.

The hydrogenation step may be carried out in a batch, semi-batch, continuous, or semi-continuous manner using any suitable reaction vessel or apparatus wherein the overhead stream may be intimately contacted with the transition metal hydrogenation catalyst and hydrogen. As the catalyst is normally heterogeneous in nature, fixed bed or slurry-type reactors are especially convenient for use. A trickle bed system such as that described in U.S. Pat. No. 5,081,321 (incorporated herein by reference in its entirety) may also be utilized.

FIG. 1 illustrates one embodiment of the integrated epoxidation process of this invention wherein a relatively light ethylenically unsaturated substrate such as propylene is epoxidized to yield a volatile epoxide. Streams comprised of secondary alcohol pass via lines 15 and 19 into alcohol oxidation zone 1 wherein the secondary alcohol is reacted with molecular oxygen to form an oxidant stream comprised of hydrogen peroxide, ketone, and excess secondary alcohol. The molecular oxygen is provided by air or pure or diluted oxygen introduced via line 2. Excess or unreacted molecular oxygen is removed via line 3.

The oxidant mixture containing hydrogen peroxide passes from zone 1 via line 4 into oxidant distillation zone 5. In 5, the oxidant mixture is subjected to fractional distillation. Aliphatic ketone is taken overhead and into hydrogenation zone 16 via line 6. The bottoms fraction, which contains hydrogen peroxide and secondary alcohol but essentially no ketone, is introduced via line 7 into substrate epoxidation zone 8.

The ethylenically unsaturated substrate to be epoxidized is fed into zone 8 via line 9, while the titanium silicalite catalyst is introduced via line 10. Alternatively, the titanium silicalite may be deployed in zone 8 as a fixed bed. The resulting reaction mixture is maintained at a temperature of from 40° C. to 120° C. in zone 8 for a time sufficient to convert at least a portion of the substrate to epoxide, thereby consuming most of the hydrogen peroxide (preferably, more than 99% of the hydrogen peroxide is consumed). The crude epoxidation product thus obtained passes through line 11 to epoxide purification zone 12 where it is separated by fractional distillation or other such means into a recycled ethylenically unsaturated substrate stream (returned to feed line 9 or substrate epoxidation zone 8 via line 13), an epoxide stream containing the desired epoxide product (withdrawn via line 14), and an alcohol stream comprised of the secondary alcohol which served as a reaction medium during epoxidation (withdrawn via line 15). The alcohol stream may also contain water when the secondary alcohol forms an azeotrope with water. It is necessary to remove that portion of the water generated as an epoxidation co-product in excess of that present in a secondary alcohol/water azeotrope so that the water content in successive cycles does not continue to increase. Water may also, under some conditions, be removed overhead together with the substrate and/or epoxide. More preferably, however, the excess water is removed via line 21 as a bottoms product following distillation of the secondary alcohol/water azeotrope. A heavies stream containing substances having boiling points higher than water may be separated from the aforementioned bottoms product by distillation.

The aforementioned fractionation may, if desired, be carried out in stages. For example, if the substrate is propylene and the epoxide is propylene oxide, both the propylene and propylene oxide may be first separated together from the secondary alcohol by an initial distillation and then further fractionated into individual substrate and epoxide streams.

The overhead stream from the oxidant distillation zone is passed via line 6 to hydrogenation zone 16 wherein the stream is reacted with hydrogen (introduced via line 17) in the presence of a suitable hydrogenation catalyst such as a supported platinum, nickel, chromium, ruthenium, rhodium or palladium catalyst (introduced via line 18 or deployed as a fixed bed in zone 16) so as to convert at least a portion, and preferably substantially all (e.g., over 95%), of the ketone back to secondary alcohol. A portion of the hydrogenated stream exiting zone 16 may advantageously be fed to substrate epoxidation zone 8 via line 20 to dilute the hydrogen peroxide to the desired concentration (preferably, 3 to 15 weight percent). The remainder (or, alternatively, all) of the hydrogenated stream produced in zone 16 is passed via line 19 to alcohol oxidation zone 1. This integrated process is preferably operated in a continuous manner such that the desired epoxide is the only major organic product and the ketone and the secondary alcohol are recycled.

From the foregoing description, one skilled in the art can readily ascertain the essential characteristics of this invention, and, without departing from the spirit and scope thereof, can make various changes and modifications of the invention to adapt it to various usages, conditions, and embodiments.

We claim:

1. An integrated process for producing an epoxide comprising the steps of
   (a) contacting an aliphatic secondary alcohol selected from isopropanol and sec-butanol with molecular oxygen in a liquid phase at a temperature of 50° to 200° C. to form an oxidant mixture comprised of 40 to 90 weight percent aliphatic secondary alcohol, 5 to 35 weight percent of an aliphatic ketone corresponding to said aliphatic secondary alcohol, 1 to 20 weight percent hydrogen peroxide, and 0 to 35 weight percent water;
   (b) separating substantially all of the aliphatic ketone from the oxidant mixture so as to provide a hydrogen peroxide-containing stream comprised of hydrogen peroxide, aliphatic secondary alcohol, less than 1 weight percent aliphatic ketone, and less than 0.5 weight percent aliphatic ketone peroxides;
   (c) reacting the aliphatic ketone separated in step (b) with hydrogen in the presence of a heterogeneous hydrogenation catalyst wherein said hydrogenation catalyst is comprised of a transition metal selected from palladium, platinum, ruthenium, chromium, rhodium and nickel at a temperature of 20° to 175° C. and a hydrogen pressure of 0.5 to 100 atmospheres to convert the aliphatic ketone to the aliphatic secondary alcohol and recycling at least a portion of the aliphatic secondary alcohol for use in step (a);
   (d) contacting the hydrogen peroxide-containing stream with an ethylenically unsaturated substrate and a catalytically effective amount of a titanium silicalite at a temperature of from 40° C. to 120° C. wherein the molar ratio of substrate:hydrogen peroxide is from 1:2 to 10:1, to form an epoxidation reaction mixture comprised of aliphatic secondary alcohol, epoxide, and water and (e) separating the aliphatic secondary alcohol present in the epoxidation reaction mixture from the epoxide and recycling at least a portion of the aliphatic secondary alcohol for use in step (a).

2. The process of claim 1 wherein the ethylenically unsaturated substrate is a $C_2$–$C_{10}$ aliphatic olefin.

3. The process of claim 1 wherein the aliphatic secondary alcohol is isopropanol.

4. The process of claim 1 wherein the titanium silicalite has an MFI, MEL, or zeolite beta topology.

5. The process of claim 1 wherein the titanium silicalite has a composition corresponding to the chemical formula $$xTiO_2:(1-x)SiO_2$$

wherein x is between 0.01 and 0.125.

6. The process of claim 1 wherein said process is carried out continuously.

7. The process of claim 1 wherein the titanium silicalite is deployed in the form of a fixed bed.

8. The process of claim 1 wherein the titanium silicalite is deployed in the form of a slurry.

9. The process of claim 1 wherein the epoxide is propylene oxide.

10. The process of claim 1 wherein separation step (b) is accomplished by distillation whereby substantially all of the aliphatic ketone is vaporized and removed from the oxidant mixture as an overhead stream.

11. The process of claim 1 wherein separation step (e) is accomplished by fractional distillation.

12. A continuous integrated process for producing propylene oxide comprising the steps of
(a) contacting an azeotrope of water and an aliphatic secondary alcohol selected from isopropanol and sec-butanol with molecular oxygen in a liquid phase at a temperature of 50° to 200° C. to form an oxidant mixture comprised of 40 to 90 weight percent aliphatic secondary alcohol, 5 to 35 weight percent of an aliphatic ketone corresponding to said aliphatic secondary alcohol, 1 to 20 weight percent hydrogen peroxide, and up to 35 weight percent water;
(b) subjecting the oxidant mixture to fractional distillation whereby substantially all of the aliphatic ketone is vaporized and removed from the oxidant mixture as an overhead stream so as to provide a bottoms fraction comprised of hydrogen peroxide, aliphatic secondary alcohol, less than 1 weight percent aliphatic ketone, and less than 0.5 weight percent aliphatic ketone peroxides;
(c) reacting the overhead stream with from 1 to 4 moles of hydrogen per mole of ketone in the overhead stream in the presence of a heterogeneous hydrogenation catalyst wherein said hydrogenation catalyst is comprised of a transition metal selected from ruthenium and nickel at a temperature of 75° to 150° C. to convert the aliphatic ketone in the overhead stream to the aliphatic secondary alcohol and recycling at least a portion of the aliphatic secondary alcohol for use in step (a);
(d) contacting the bottoms fraction with propylene and a catalytically effective amount of a titanium silicalite at a temperature of from 50° to 110° C. to convert the propylene to propylene oxide, wherein the molar ratio of olefin: hydrogen peroxide is from 1:2 to 10:1, to form an epoxidation reaction mixture comprised of aliphatic secondary alcohol, propylene oxide and water.
(e) removing the propylene oxide from the epoxidation reaction mixture by fractional distillation; and
(f) removing the aliphatic secondary alcohol and at least a portion of the water as an azeotrope from the epoxidation reaction mixture by distillation and recycling the azeotrope for use in step (a).

* * * * *